United States Patent
Kopp et al.

(10) Patent No.: US 12,048,827 B2
(45) Date of Patent: Jul. 30, 2024

(54) COUPLING ELEMENT FOR A CLOSED FLUID TRANSFER SYSTEM, COUNTER COUPLING ELEMENT FOR A COUPLING ELEMENT OF THIS TYPE, AND COUPLING SYSTEM

(71) Applicant: B. Braun Melsungen AG, Melsungen (DE)

(72) Inventors: Florin Kopp, Schortens (DE); Karl Martin Berg, Melsungen (DE); Konstantin Krug-Sauer, Gudensberg (DE); Johannes Bolz, Kassel (DE)

(73) Assignee: B. Braun Melsungen AG, Melsungen (DE)

( * ) Notice: Subject to any disclaimer, the term of this patent is extended or adjusted under 35 U.S.C. 154(b) by 43 days.

(21) Appl. No.: 17/907,995

(22) PCT Filed: Mar. 3, 2021

(86) PCT No.: PCT/EP2021/055249
§ 371 (c)(1),
(2) Date: Aug. 30, 2022

(87) PCT Pub. No.: WO2021/175884
PCT Pub. Date: Sep. 10, 2021

(65) Prior Publication Data
US 2023/0092208 A1     Mar. 23, 2023

(30) Foreign Application Priority Data
Mar. 6, 2020   (DE) ..................... 10 2020 202 935.0

(51) Int. Cl.
*A61M 39/10*   (2006.01)
*A61M 5/14*    (2006.01)
(Continued)

(52) U.S. Cl.
CPC .......... *A61M 5/1413* (2013.01); *A61M 5/162* (2013.01); *A61M 39/10* (2013.01);
(Continued)

(58) Field of Classification Search
CPC ................ A61M 39/165; A61M 39/16; A61M 2039/1072; A61M 39/26;
(Continued)

(56) References Cited

U.S. PATENT DOCUMENTS 5,061,264 A    10/1991  Scarrow
5,122,123 A *  6/1992   Vaillancourt ......... A61M 39/14
                                                        604/905
(Continued)

FOREIGN PATENT DOCUMENTS

AU    2013200393 B2    5/2014
AU    2014277764 A1    1/2015
(Continued)

OTHER PUBLICATIONS

Search Report received in German Application No. 10 2020 202 935.0 dated Nov. 23, 2020, with translation, 14 pages.
(Continued)

*Primary Examiner* — David Colon-Morales
(74) *Attorney, Agent, or Firm* — Christopher A. Rothe; Culhane PLLC

(57) ABSTRACT

A coupling member for a closed fluid transfer system includes a housing having a fluid connection and a coupling side. The housing includes a longitudinal axis extending from the fluid connection toward the coupling side and a spike having a fluid opening. The fluid opening is arranged in an end portion of the spike facing the coupling side. A sealing member receptacle is arranged in the housing on the coupling side, and a sealing member is arranged in the sealing member receptacle. The housing includes a housing
(Continued)

portion that at least partially surrounds the sealing member receptacle and a threaded portion. The coupling housing with the sealing member is guided by a guiding structure and movable in the direction of the longitudinal axis via the threaded portion between a position with maximum distance to the fluid connection and a position with minimum distance to the fluid connection.

19 Claims, 6 Drawing Sheets

(51) Int. Cl.
  *A61M 5/162* (2006.01)
  *A61M 39/26* (2006.01)
  *F16L 37/46* (2006.01)
(52) U.S. Cl.
  CPC ...... *F16L 37/46* (2013.01); *A61M 2039/1027* (2013.01); *A61M 2039/1072* (2013.01); *A61M 2039/267* (2013.01); *F16L 2201/44* (2013.01)
(58) Field of Classification Search
  CPC ........ A61M 2039/267; A61M 39/1011; A61M 5/1413; A61M 5/162; A61M 39/10; A61M 2039/1027; A61M 2039/1066; A61M 2039/1033; F16L 37/46; F16L 2201/44
  See application file for complete search history.

(56) References Cited

U.S. PATENT DOCUMENTS

| | | | |
|---|---|---|---|
| 5,201,717 A | 4/1993 | Wyatt et al. | |
| 5,514,117 A * | 5/1996 | Lynn | A61M 5/3213 604/536 |
| 7,004,934 B2 | 2/2006 | Vaillancourt | |
| 7,080,672 B2 | 7/2006 | Fournie et al. | |
| 7,137,654 B2 | 11/2006 | Segal et al. | |
| 7,396,051 B2 | 7/2008 | Baldwin et al. | |
| 7,497,848 B2 | 3/2009 | Leinsing et al. | |
| 7,628,781 B2 | 12/2009 | Roy et al. | |
| 8,196,614 B2 | 6/2012 | Kriheli | |
| 8,262,641 B2 | 9/2012 | Vedrine et al. | |
| 8,267,127 B2 | 9/2012 | Kriheli | |
| 8,287,513 B2 | 10/2012 | Ellstrom et al. | |
| 8,870,832 B2 | 10/2014 | Raday et al. | |
| 8,910,919 B2 * | 12/2014 | Bonnal | A61M 39/1011 604/533 |
| 8,915,902 B2 | 12/2014 | Reynolds et al. | |
| 8,926,583 B2 | 1/2015 | Ellstrom et al. | |
| 9,039,047 B2 | 5/2015 | Imai | |
| 9,345,643 B2 | 5/2016 | Okiyama | |
| 9,370,466 B2 | 6/2016 | Garfield et al. | |
| 9,493,281 B2 | 11/2016 | Ohlin et al. | |
| 9,510,997 B2 | 12/2016 | Kriheli et al. | |
| 9,541,227 B2 | 1/2017 | Okiyama | |
| 9,549,873 B2 | 1/2017 | Barrelle et al. | |
| 9,579,258 B2 | 2/2017 | Fukuoka | |
| 9,636,278 B2 | 5/2017 | Sanders et al. | |
| 9,642,775 B2 | 5/2017 | Sanders et al. | |
| 9,724,504 B2 | 8/2017 | Fangrow, Jr. et al. | |
| 9,775,979 B2 | 10/2017 | Okiyama | |
| 9,820,913 B2 | 11/2017 | Genosar | |
| 9,855,192 B2 | 1/2018 | Kim et al. | |
| 9,877,895 B2 | 1/2018 | Garfield et al. | |
| 9,933,094 B2 * | 4/2018 | Fangrow | A61M 39/26 |
| 9,951,899 B2 | 4/2018 | Py et al. | |
| 9,974,939 B2 | 5/2018 | Fangrow, Jr. | |
| 9,987,477 B2 | 6/2018 | Winsor | |
| 9,993,636 B2 | 6/2018 | Uber, III et al. | |
| 9,999,569 B2 | 6/2018 | Kriheli | |
| 10,022,301 B2 | 7/2018 | Ivosevic et al. | |
| 10,022,531 B2 | 7/2018 | Shemesh | |
| 10,058,693 B2 | 8/2018 | Phillips et al. | |
| 10,137,237 B2 | 11/2018 | Bengtsson et al. | |
| 10,156,306 B2 | 12/2018 | Fangrow | |
| 10,206,853 B2 * | 2/2019 | Sanders | A61J 1/2096 |
| 10,206,854 B2 | 2/2019 | Wu et al. | |
| 10,335,536 B2 | 7/2019 | Melander et al. | |
| 10,357,430 B2 | 7/2019 | Kriheli et al. | |
| 10,376,654 B2 | 8/2019 | Sanders et al. | |
| 10,398,627 B2 | 9/2019 | Kriheli | |
| 10,441,507 B2 | 10/2019 | Sanders | |
| 10,456,329 B2 | 10/2019 | Sanders et al. | |
| 10,470,974 B2 | 11/2019 | Sanders et al. | |
| 10,518,078 B2 | 12/2019 | Bejhed et al. | |
| 10,561,802 B2 | 2/2020 | Kim et al. | |
| 10,632,044 B2 | 4/2020 | Garfield et al. | |
| 10,682,505 B2 | 6/2020 | Shemesh | |
| 10,894,317 B2 | 1/2021 | Garfield et al. | |
| 10,945,922 B1 | 3/2021 | Cairns | |
| 2007/0066965 A1 * | 3/2007 | Coambs | A61M 39/14 604/533 |
| 2008/0097371 A1 | 4/2008 | Shemesh | |
| 2009/0035383 A1 | 2/2009 | Ohta et al. | |
| 2009/0069783 A1 | 3/2009 | Ellstrom et al. | |
| 2009/0299295 A1 | 12/2009 | Rubinstein et al. | |
| 2011/0106046 A1 * | 5/2011 | Hiranuma | A61M 39/04 604/414 |
| 2011/0282298 A1 | 11/2011 | Agian et al. | |
| 2013/0006211 A1 | 1/2013 | Takemoto | |
| 2013/0072893 A1 | 3/2013 | Takemoto | |
| 2013/0076019 A1 * | 3/2013 | Takemoto | A61J 1/2096 285/117 |
| 2013/0144246 A1 * | 6/2013 | Takemoto | A61M 39/1011 604/403 |
| 2013/0296791 A1 | 11/2013 | Segev et al. | |
| 2014/0263322 A1 | 9/2014 | Ghodbane et al. | |
| 2015/0123398 A1 | 5/2015 | Sanders et al. | |
| 2015/0126958 A1 | 5/2015 | Sanders et al. | |
| 2015/0126974 A1 | 5/2015 | Sanders et al. | |
| 2016/0008544 A1 | 1/2016 | Molson et al. | |
| 2017/0209682 A1 | 7/2017 | Shemesh | |
| 2018/0000690 A1 | 1/2018 | Eichelkraut et al. | |
| 2018/0028402 A1 | 2/2018 | Kriheli et al. | |
| 2018/0161245 A1 | 6/2018 | Kriheli | |
| 2018/0200147 A1 | 7/2018 | Sanders | |
| 2018/0200148 A1 | 7/2018 | Sanders | |
| 2018/0200498 A1 | 7/2018 | Sanders | |
| 2019/0000718 A1 | 1/2019 | Kriheli et al. | |
| 2019/0046410 A1 | 2/2019 | Shemesh | |
| 2019/0053980 A1 | 2/2019 | West et al. | |
| 2019/0060171 A1 | 2/2019 | Lee | |
| 2019/0184152 A1 * | 6/2019 | Kakinoki | A61M 39/1011 |
| 2019/0290543 A1 | 9/2019 | McKinnon et al. | |
| 2019/0321261 A1 | 10/2019 | Oshinski et al. | |
| 2020/0323734 A1 | 10/2020 | Ueda et al. | |
| 2022/0260189 A1 | 8/2022 | Deuse | |

FOREIGN PATENT DOCUMENTS

| | | |
|---|---|---|
| DE | 102019116970 A1 | 12/2020 |
| EP | 2589368 A1 | 5/2013 |
| EP | 3067037 A1 | 9/2016 |
| EP | 3517164 A1 | 7/2019 |
| EP | 3607993 A1 | 2/2020 |
| IL | 214990 A | 6/2013 |
| IL | 257415 B | 1/2020 |
| IL | 257417 B | 11/2020 |
| WO | 2008129550 A2 | 10/2008 |
| WO | 2009035383 A1 | 3/2009 |
| WO | 2011150037 A1 | 12/2011 |
| WO | 2012117648 A1 | 9/2012 |
| WO | 2014122643 A1 | 8/2014 |
| WO | 2014181320 A1 | 11/2014 |
| WO | 2015017858 A1 | 2/2015 |
| WO | 2015069643 A1 | 5/2015 |
| WO | 2016042544 A1 | 3/2016 |
| WO | 2016199133 A1 | 12/2016 |
| WO | 2017066406 A1 | 4/2017 |
| WO | 2017109776 A1 | 6/2017 |

(56) References Cited

FOREIGN PATENT DOCUMENTS

| WO | 2017183031 | A1 | 10/2017 | | |
|----|-----------|----|---------|---|---|
| WO | 2019033004 | A1 | 2/2019 | | |
| WO | 2019086589 | A1 | 5/2019 | | |
| WO | 2019086589 | A1 | 5/2019 | | |
| WO | 2019135219 | A2 | 7/2019 | | |
| WO | 2019135219 | A2 | 7/2019 | | |
| WO | 2019167035 | A1 | 9/2019 | | |
| WO | 2019187839 | A1 | 10/2019 | | |
| WO | WO-2019187839 | A1 * | 10/2019 | ............. | A61J 1/201 |
| WO | 2020031174 | A1 | 2/2020 | | |
| WO | 2020031174 | A1 | 2/2020 | | |
| WO | 2021019532 | A1 | 2/2021 | | |

OTHER PUBLICATIONS

Search Report received in International Application No. PCT/EP2021/055249 dated Jun. 11, 2021, with translation, 5 pages.
Written Opinion received in International Application No. PCT/EP2021/055249 dated Jun. 11, 2021, with translation, 18 pages.
Office Action received in Chinese Application No. 202180017871.2 dated Sep. 26, 2023, with translation, 11 pages.

* cited by examiner

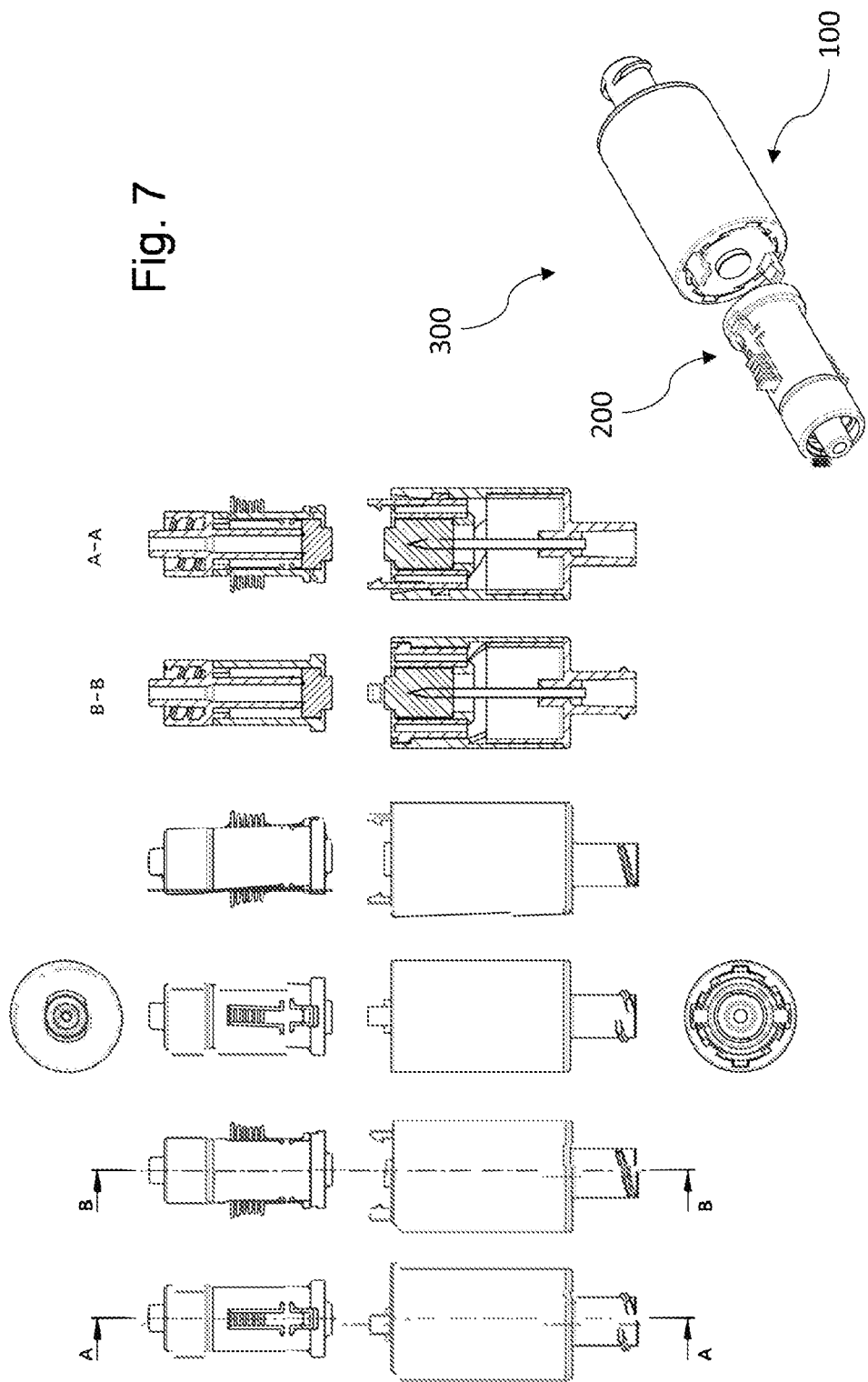

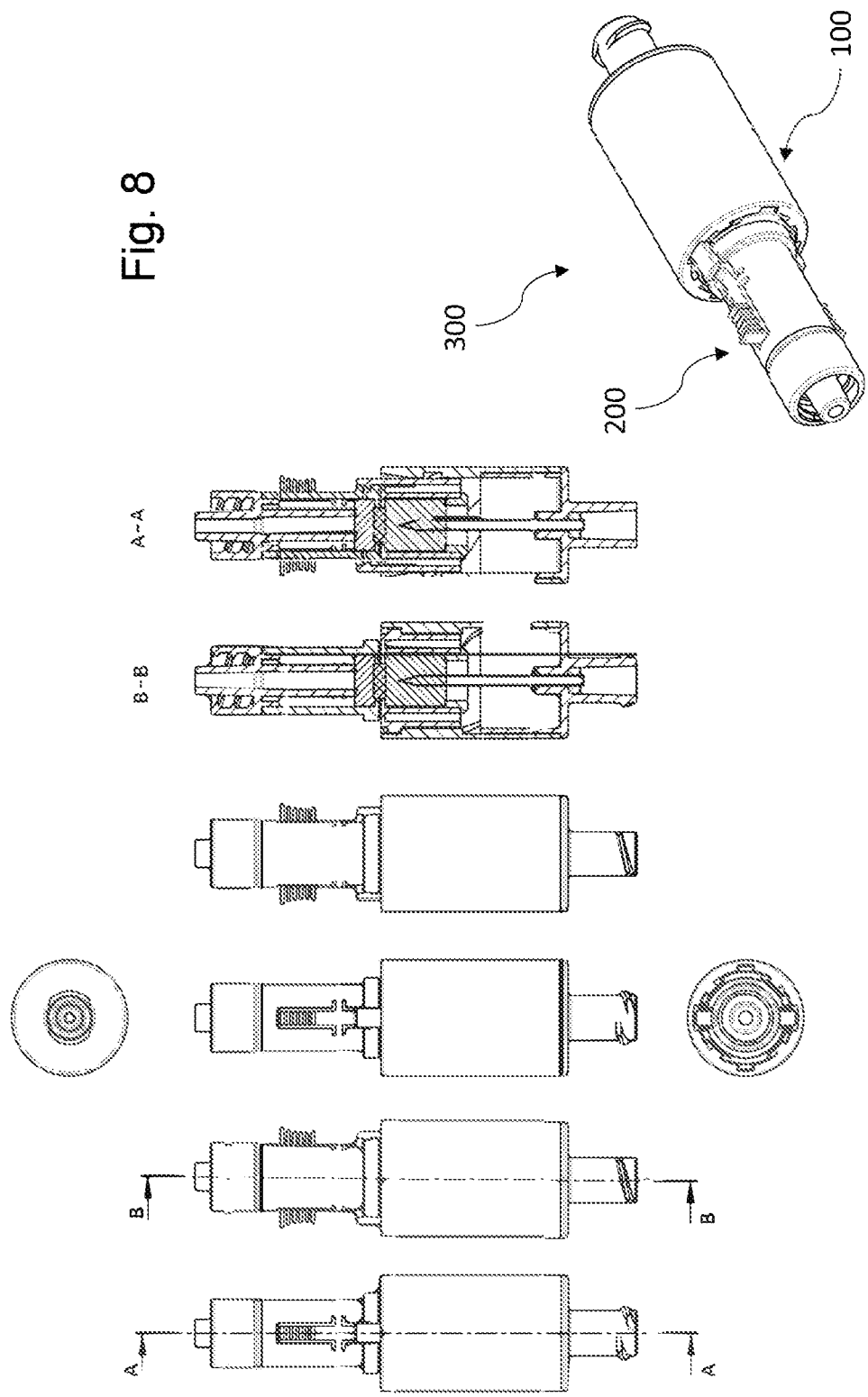

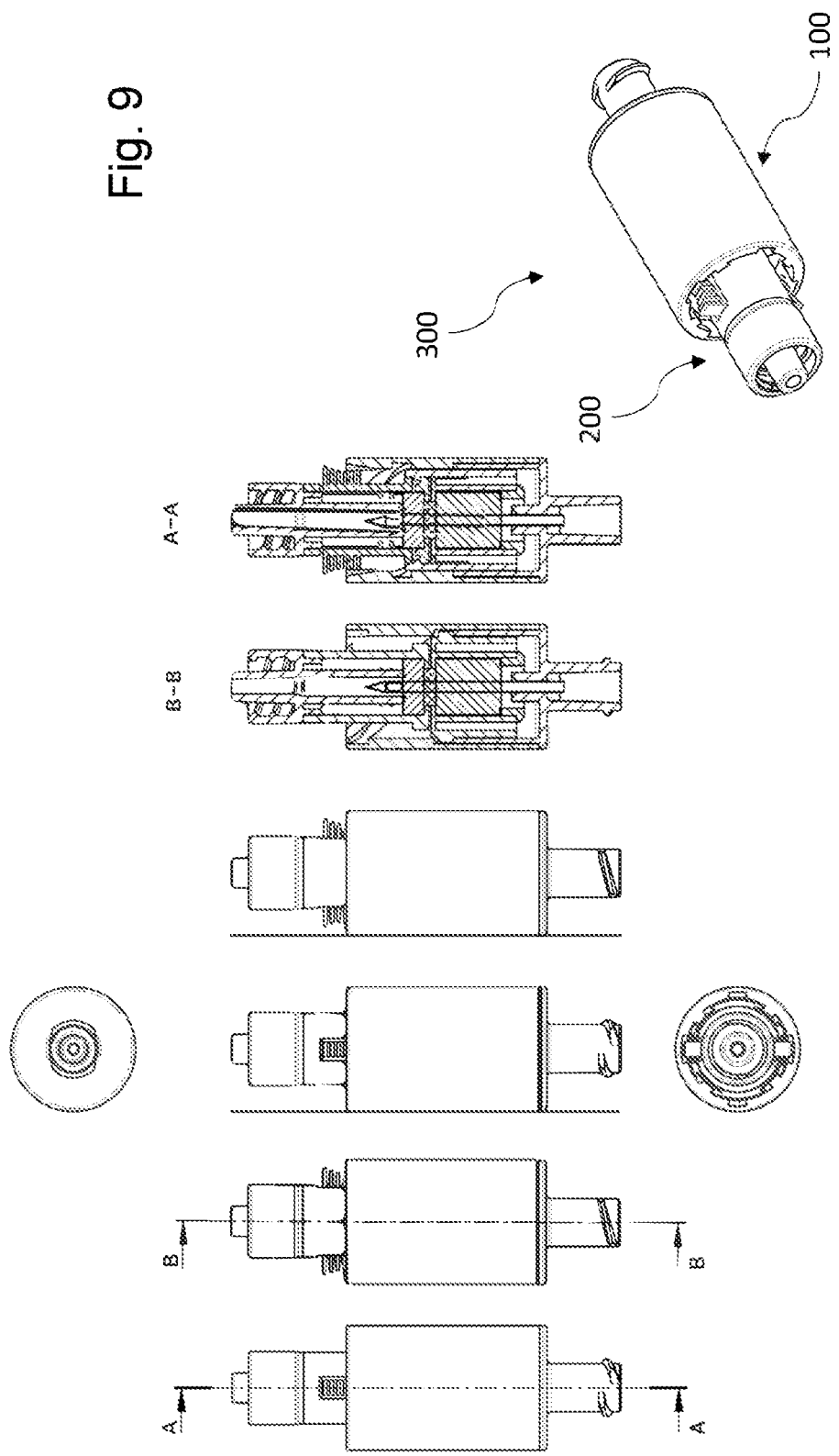

COUPLING ELEMENT FOR A CLOSED FLUID TRANSFER SYSTEM, COUNTER COUPLING ELEMENT FOR A COUPLING ELEMENT OF THIS TYPE, AND COUPLING SYSTEM

CROSS-REFERENCE TO RELATED APPLICATIONS

This application is the United States national stage entry of International Application No. PCT/EP2021/055249, filed Mar. 3, 2021, and claims priority to German Application No. 10 2020 202 935.0, filed Mar. 6, 2020. The contents of International Application No. PCT/EP2021/055249 and German Application No. 10 2020 202 935.0 are incorporated by reference herein in their entireties.

FIELD

The invention relates to a coupling member for a closed fluid transfer system, a mating coupling member for such coupling member, and a coupling system.

BACKGROUND

Many substances that are administered as injections or in a comparable form of delivery, such as CMR drugs, which are used in cancer therapy, for example, and whose therapeutic application is primarily aimed at damaging growth-intensive tumor cells, have a considerable hazard potential outside the actual therapeutic application. Due to their mechanism of action, some of these substances are themselves carcinogenic, which is why contact with persons not undergoing therapy must be avoided. Closed drug transfer systems, so called "closed system transfer devices" or CSTDs, are therefore increasingly being used for CMR drugs in the manufacture of ready-to-use preparations. An important component of such CSTDs are coupling systems that enable the safe transfer of CMR drugs or other substances and dry seal after disconnection, thus protecting the environment from contamination, e.g. through leakage or droplet formation on the surfaces of the coupling members.

Coupling systems of this type are, in general, associated with the terms "dry connection", "automatic self-sealing technology" or "closed connection" and are essential for the realization of closed fluid transfer systems.

Known coupling systems are often complex with respect to their handling and connection structures and may provide poor flow rates. Furthermore, fluid residues may occur on the sealing surfaces and coupling surfaces, respectively, if a constant surface pressure of the sealing surfaces is not maintained.

All current systems have in common, that they are comparably large, which results in disadvantages during an application near a patient, and that at least a coupling member or a mating coupling member provides poor accessibility of the coupling and mating coupling surface, respectively, due to their structure so that disinfection is hampered.

SUMMARY

In view of the disadvantages associated with the prior art, it is the object of the present invention to provide a coupling member, a mating coupling member and a coupling system for a closed fluid transfer system, in which the respective coupling surfaces are dry-locked in the disconnected state and are capable of being handled safely in a simple manner.

According to the invention, the coupling member for a closed fluid transfer system comprises a coupling member housing comprising a fluid connection and a coupling side, wherein the coupling member housing comprises a longitudinal axis extending from the fluid connection toward the coupling side, a spike comprising at least one fluid opening and retained in a spike receptacle of the housing disposed at the fluid connection and extending in the direction of the longitudinal axis into the coupling member housing, wherein the at least one fluid opening is arranged in an end portion of the spike facing the coupling side, a sealing member receptacle arranged in the coupling member housing on the coupling side, and a sealing member arranged in the sealing member receptacle, wherein the coupling housing comprises a housing portion, which at least partially surrounds the sealing member receptacle in an axial direction with respect to the longitudinal axis and comprises a coupling housing threaded portion on the inner surface facing the sealing member, and wherein the coupling housing with the sealing member is, guided by a sealing member receptacle guiding structure, movable in the direction of the longitudinal axis via the coupling housing threaded portion between a position with maximum distance to the fluid connection and a position with minimum distance to the fluid connection.

Due to the interaction of the sealing member receptacle guiding structure with the coupling housing threaded portion, the sealing member receptacle can be secured against an unintended movement by pure compression or tensile forces. The position with maximum distance to the fluid connection corresponds to a position of the sealing member receptacle in a disconnected state, while the position with minimum distance to the fluid connection is preferably present, when a connected state is reached, which is intended for a fluid communication with a mating coupling member.

The term "thread" with respect to the coupling housing threaded portion or also hereinafter is not limited to an isometric thread or a thread with oblique thread flanks, but comprises, in general, a structural design, in which a guiding structure is formed helically.

In particular, the at least one fluid opening is arranged in the sealing member, when the sealing member receptacle with the sealing member is located in the position with maximum distance to the fluid connection.

Thus, with respect to the above reduction of the risk of an unintended movement, the leakage of fluid in a disconnected state can be prevented.

In an embodiment, the coupling housing threaded portion is formed as female thread, and the sealing member receptacle guiding structure comprises at least one projection engageable in the female thread projecting radially outward with respect to the longitudinal axis.

The sealing member receptacle guiding structure can thereby be formed in a simple manner. In principle, it is also possible to form the coupling housing threaded portion as a male thread, wherein the sealing member receptacle guiding structure is at least partially formed as a female thread corresponding thereto.

In particular, the coupling housing threaded portion comprises at least two threads separated from each other, in particular at least two threads opposing each other.

In conjunction with at least two sealing member receptacle guiding structures respectively opposing each other, the sealing member receptacle may be guided in a more stable position in the coupling housing threaded portion, since a tilting of the sealing member receptacle is thereby prevented. The number of threads may, however, also be less than the number of sealing member receptacle guiding structures, for example, to insert the sealing member receptacle into the coupling housing in different orientations and/or to provide different movements of the sealing member receptacle by different threads.

In an embodiment, at least one thread of the coupling housing threaded portion extends over an angle of less than 360° with respect to the longitudinal axis, in particular over an angle of substantially 180°.

The guided movement of the sealing member receptacle may thereby be carried out over a limited angle of rotation, which eases handling. Furthermore, a shortened angle of rotation, i.e. an angle of rotation for reaching a target position, which does not comprise several rotations, facilitates the control of movement, since several rotations do not have to be tracked. In this context, optical or haptic marking elements may support the motion control.

In a further development, at least one thread of the coupling housing threaded portion comprises, at its end facing the fluid connection, an orthogonal portion with respect to the longitudinal axis.

Hence, the inclination of the thread is not continued via this portion. When the sealing member receptacle guiding structure is moved into the orthogonal portion, the sealing member receptacle cannot be moved out of this position by the application of pure tensile or compression forces in the direction of the longitudinal axis. Accordingly, the orthogonal portion allows a securing of the positioning of the sealing member receptacle in this position, in particular in the position with minimum distance to the fluid connection, if the orthogonal portion corresponds to this position.

In particular, at least one thread of the coupling housing threaded portion comprises, at its end facing the fluid connection, a recessed portion toward the longitudinal axis, which is recessed in the direction of the coupling side with respect to the thread.

When the sealing member receptacle guiding structure is moved into the recessed portion, the sealing member receptacle cannot be moved out of this position by applying pure rotational movements about the longitudinal axis, but has to be initially moved out of the recessed portion along the longitudinal axis toward the fluid connection by applying a compression force on the sealing member receptacle. The position of the sealing member receptacle guiding structure in the recessed portion corresponds preferably to a position of the sealing member receptacle in the connected state. The recessed portion may be provided alternatively or in addition to the orthogonal portion. In a combination of the recessed and orthogonal portion, the recessed portion preferably adjoins the orthogonal portion in the guiding direction of the sealing member receptacle guiding structure at an end of the thread facing the fluid connection. For example, the sealing member receptacle guiding structure is first moved toward the fluid connection along the at least one thread providing an inclination, then reaches the orthogonal portion, and may be subsequently moved into the recessed portion by a continued rotational movement.

In an embodiment, the housing portion is rotatable relative to the longitudinal axis.

Thus, the sealing member receptacle may be moved along the longitudinal axis by a rotational movement of the housing portion about the longitudinal axis via the sealing member receptacle guiding structure. Preferably, the housing portion is a portion rotatably supported relative to the rest of the housing, such that the rotational movement performed by the housing portion is not transmitted to the rest of the housing. This facilitates handling or connection and disconnection, in particular, if, for example, further components are already connected to the fluid connection.

Alternatively or in addition, the sealing member receptacle is rotatable relative to the longitudinal axis and/or to the coupling member housing.

Accordingly, not or not only the housing portion is rotated for moving the sealing member receptacle via the sealing member receptacle guiding structure in engagement with at least a corresponding thread, but the sealing member receptacle.

According to a further development, the sealing member receptacle, together with the sealing member, forms at least a part of the coupling side front surface of the coupling member.

The sealing member receptacle and the sealing member are thus not set back, so that they provide a good accessibility, whereby a disinfection is facilitated. In particular, the coupling side front surface may be designed substantially flat. The term "substantially flat" is directed to the fact that minor contour deviations, such as a central elevation by the sealing member, may be formed, but these have no influence on the coupling side front surface of the coupling member in terms of accessibility.

In particular, the sealing member receptacle comprises, at its end facing the coupling side, a coupling member side fastening structure for a mating coupling member, in particular at least two snap hooks projecting in the direction of the longitudinal axis toward the coupling side.

By the coupling member side fastening structure at the sealing member receptacle, it may be ensured that a mating coupling member fastened thereto is retained in a predetermined positional relationship during movement of the sealing member receptacle from a position with maximum distance to the fluid connection and minimum distance to the fluid connection along the longitudinal axis. In particular, such a predetermined positional relationship provides a constant surface pressure between the sealing member and the mating coupling member sealing member, such that a fluid tightness may be ensured. In other words, a constant surface pressure of the elastomer surfaces is achieved over the entire connecting path. Preferably, the fastening structure is designed, such that the fastening of the mating coupling member to the fastening structure is only carried out by applying compression forces in the direction of the coupling member and/or mating coupling member and no rotational movement is executed to not move the sealing member receptacle along the thread already during the fastening procedure. If the fastening procedure comprises a rotational movement, this should be at least opposite to the rotational movement for moving the sealing member receptacle along the thread.

For example, the use of snap hooks as fastening structure implements a fastening by a compression force in a simple manner. Further, snap hooks do hardly interfere the accessibility to the coupling side front surface such that a disinfection is still easily possible. Furthermore, a tilting of the mating coupling member may be prevented by at least two snap hooks, which are preferably arranged opposite to each other.

According to a further development, the sealing member receptacle is supported in the coupling member housing by an elastic member, in particular a compression spring member, which acts in the direction of the longitudinal axis and is arranged between the fluid connection and the sealing member receptacle.

The elastic member may be formed by a separate spring member or by the sealing member or the sealing member receptacle. If the elastic member is formed by the sealing member or the sealing member receptacle, this member is integrated into the respective component or is formed thereby, for example, by a respective material selection and/or structural design. In such event, the sealing member or the sealing member receptacle is supported against the coupling member housing in the longitudinal direction, in the same way as a separate spring member. The sealing member receptacle is retained in a position with maximum distance to the fluid connection by the elastic member without the application of an external force. Accordingly, a movement of the sealing member receptacle toward the fluid connection requires the retaining force to be overcome, so that the risk of an unintended movement is reduced. Further, the elastic member supports a return movement from a connected state to a disconnected state.

In another aspect, the invention is also directed to a coupling system für a closed fluid transfer system. The coupling system comprises at least one coupling member as previously described and at least one mating coupling member for coupling with the coupling member. The mating coupling member comprises a mating coupling member housing comprising a mating coupling member fluid connection and a mating coupling side, wherein the mating coupling member housing comprises a mating coupling member longitudinal axis extending from the mating coupling member fluid connection toward the mating coupling side, and a mating coupling member sealing member, which is arranged in the mating coupling member housing and forms, together with the mating coupling member housing, at least a part of a mating coupling side front surface of the mating coupling member. The coupling system is configured such that the fluid opening of the coupling member in a state connected to the mating coupling member, in which the sealing member receptacle is located in the position with minimum distance to the fluid connection of the coupling member, is at least partially arranged on a side of the mating coupling member sealing member of the mating coupling member facing the mating coupling member fluid connection.

Due to the movement of the sealing member receptacle from a position with maximum distance to the fluid connection into a position with minimum distance to the fluid connection and a respective movement of the mating coupling member, wherein the mating coupling side front surface of the mating coupling member sealing member and the coupling side front surface of the sealing member of the coupling member are in fluid-tight contact with each other, the sealing member of the coupling member and the mating coupling member sealing member are moved in the longitudinal direction along the spike 30 toward the fluid connection. For a fluid communication of the coupling member with the mating coupling member by the spike, the coupling system is configured such that the sealing member and the mating sealing member are moved toward the fluid connection of the coupling member to such an extent that the fluid opening of the spike of the coupling system in a connected state, in which the sealing member receptacle is located in the position with minimum distance to the fluid connection of the coupling member, projects at least partially, in particular completely, on a side of the mating coupling sealing member facing away from the mating coupling member side front surface into a mating coupling member fluid channel comprised or formed by the mating coupling member housing. Accordingly, the fluid opening is continuously sealed by the sealing member and the mating coupling sealing member until shortly before reaching the connected state. When the coupling member and the mating coupling member are disconnected, any fluid still on the spike may be wiped off at the mating coupling member sealing member, so that the risk of a fluid leakage during or after disconnection is reduced.

In an embodiment, the mating coupling member housing comprises a fastening portion, which extends from the mating coupling side in the direction of the mating coupling member longitudinal axis toward the mating coupling member fluid connection and comprises a mating coupling member side fastening structure, in particular a recess, for connection to the coupling member side fastening structure, in particular for receiving the snap hooks.

The mating coupling member side fastening structure is thus set back relative to the mating coupling side front surface when viewed from the mating coupling side, as a result of which the mating coupling side front surface of the mating coupling member sealing member may be retained with a predetermined surface pressure when the mating coupling member is fastened to the coupling member. At the same time, accessibility of the mating coupling side front surface, for example for disinfection purposes, is not limited thereby.

The mating coupling side fastening structure may be continuous radially circumferentially with respect to the mating coupling member longitudinal axis to enable the mating coupling member to be fastened to the coupling member in any relative radial position. Alternatively, the mating coupling member side fastening structure may be formed only in sections to permit corresponding fastening only in one or more predetermined relative positions. For example, in only one relative position intended for fastening, the mating coupling member side fastening structure may have recesses, whose position and dimensions correspond uniquely to the snap hooks of a coupling member.

In an embodiment, the mating coupling member housing comprises an unlocking mechanism on an external wall extending in the direction of the mating coupling member longitudinal axis, by which the connection of the mating coupling member side fastening structure to the coupling member side fastening structure is releasable.

Such an unlocking mechanism may be formed, for example, via a resilient or elastically supported mating coupling member housing portion that includes or cooperates with a portion of the mating coupling member side fastening structure so as to be movable such that a coupling member side fastening structure is movable out of the mating coupling member side fastening structure. In this regard, it is advantageous if the coupling member housing is configured such that such unlocking is prevented in a state in which the sealing member receptacle is in a position with minimal distance to the fluid connection.

Further advantages of the coupling system are furthermore analogous to the advantages cited with respect to the coupling member and/or the mating coupling member.

BRIEF DESCRIPTION OF THE DRAWING FIGURES

Features, expediencies and advantages of the invention are also described below with reference to the drawings by way of exemplary embodiments.

FIG. 7 is an overview of all external views of the coupling system according to FIGS. 4 and 5, the cross-sectional views along intersection line A-A and intersection line B-B, and a perspective view in the disconnected state;

Figure 4:
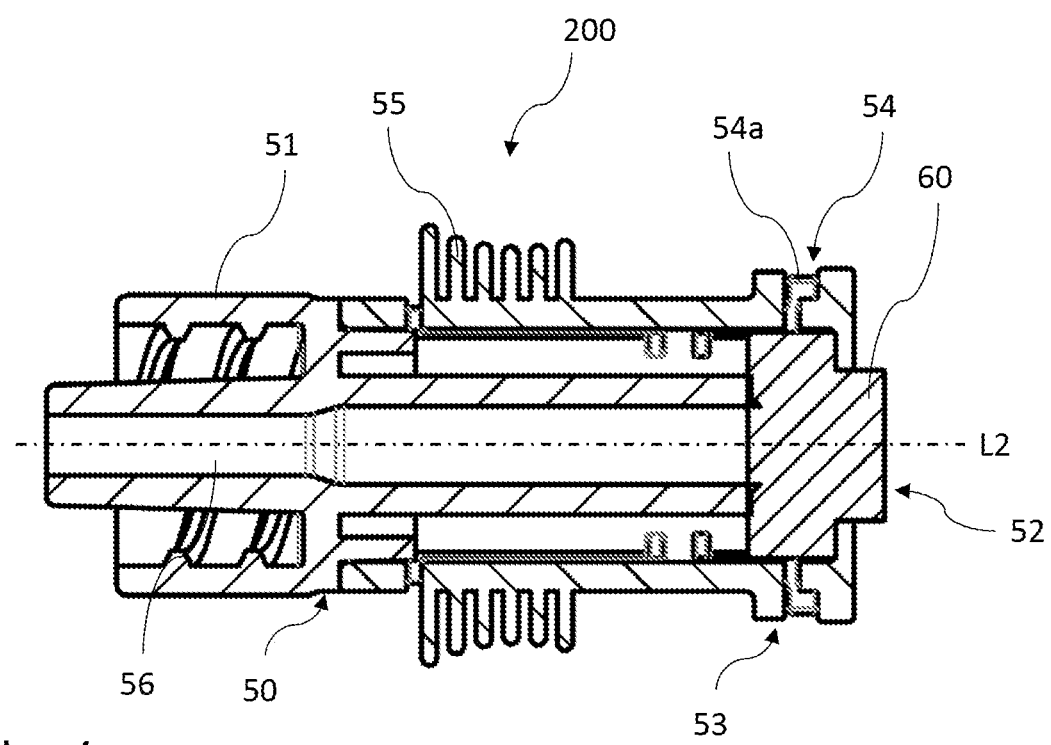
FIG. 4 is a schematic cross-sectional view of a mating coupling member in a plane parallel to the mating coupling member longitudinal axis of the mating coupling member housing according to an exemplary first embodiment of the mating coupling member in the disconnected state.
Figure 5:
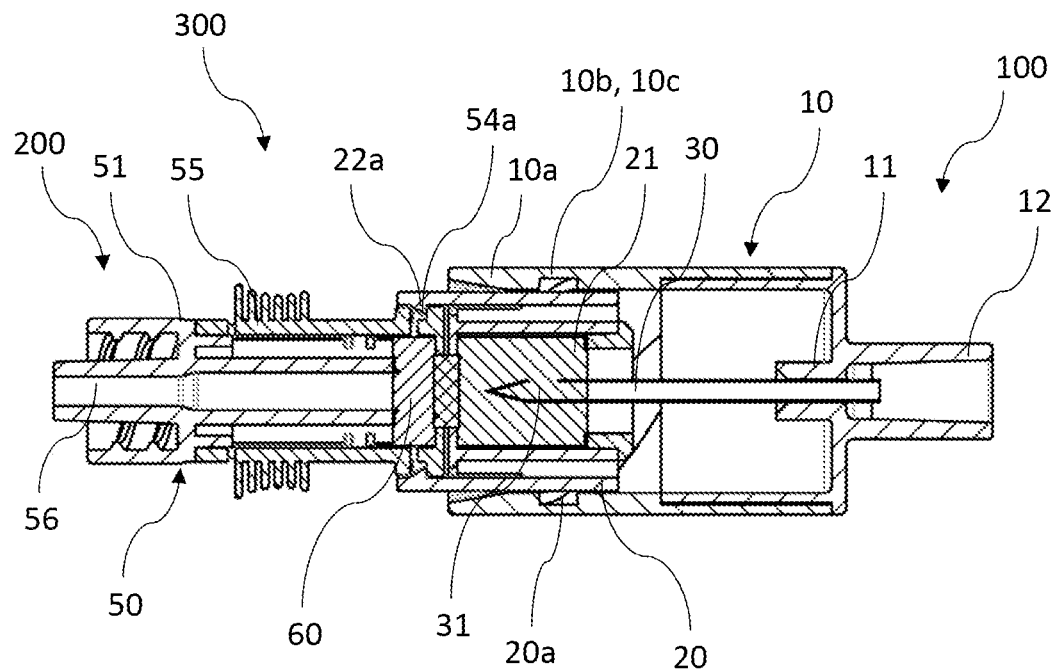
FIG. 5 is a schematic cross-sectional view of a coupling system with a coupling member according to FIG. 1 and a mating coupling member according to FIG. 4 in a plane parallel to the longitudinal axis in the disconnected state, in which the mating coupling member is retained by the coupling member.

FIG. 8 is an overview of all external views of the coupling system according to FIG. 7 or FIGS. 4 and 5, the sectional views along intersection line A-A and intersection line B-B, and a perspective view in a disconnected state in which the mating coupling member is retained by the coupling member; and FIG. 9 is an overview of all external views of the coupling system according to FIGS. 7 and 8 or FIGS. 4 and 5, the sectional views along intersection line A-A and intersection line B-B, and a perspective view in the connected state.

DETAILED DESCRIPTION

Figure 1:
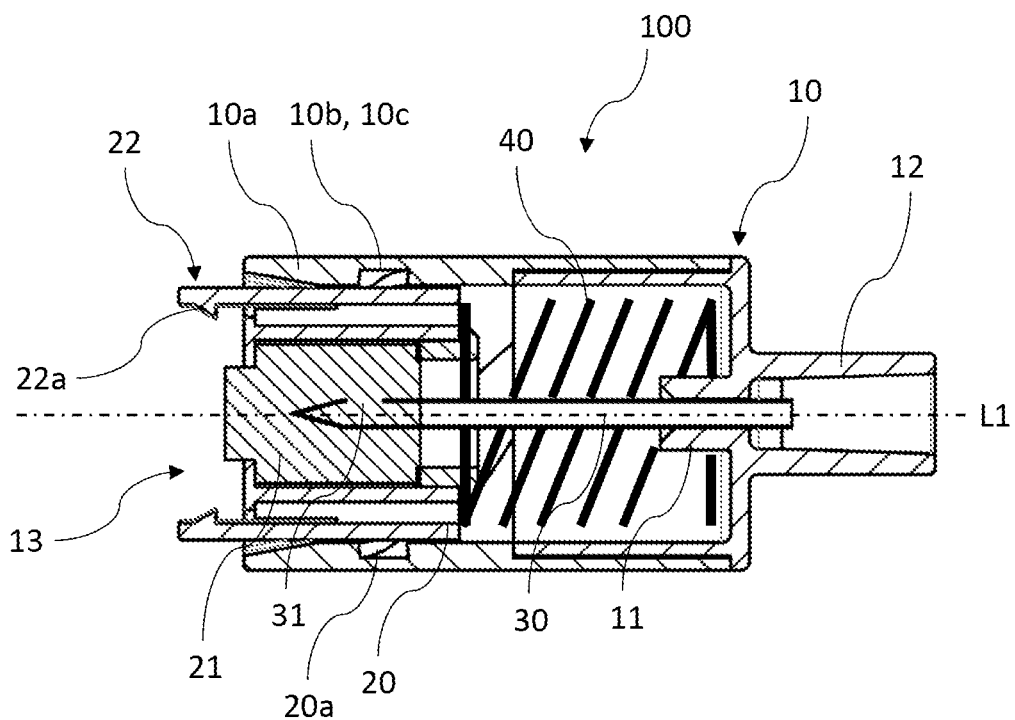
FIG. 1 is a schematic cross-sectional view of a coupling member in a plane parallel to the longitudinal axis of the coupling member housing according to an exemplary first embodiment of the coupling member in the disconnected state.

FIG. 1 shows a cross-sectional view of a coupling member 100 in a plane parallel to the longitudinal axis L1 of a coupling member housing 10 of the coupling member 100 in an exemplary first embodiment. The intersection line corresponds to the intersection line A-A of the coupling system 300 shown in FIG. 6. The longitudinal axis L1 of the coupling member 100 extends from a fluid connection 12 toward a coupling side 13. In addition to the coupling member housing 10, the coupling member 100 comprises a spike receptacle 11, a spike 30 received in the spike receptacle 11 and formed as a fluid channel, a sealing member receptacle 20 having a sealing member receptacle guiding structure 20a, a sealing member 21 received in the sealing member receptacle 20, and an elastic member 40 disposed between a fluid connection side end of the coupling member housing 10 and the sealing member receptacle 20.

The coupling member housing 10 comprises a housing portion 10a extending from the fluid connection side portion of the coupling member housing 10 toward the coupling side 13 around the longitudinal axis L1. In the embodiment shown, the housing portion 10a is preferably rotatably supported about the longitudinal axis L1. The housing portion 10a further comprises a coupling housing threaded portion 10b having two threads 10c, wherein, however, more or less threads 10c may be provided. The threads 10c are each formed here as helical grooves extending from the coupling side 13 toward the fluid connection 12 over an angle of 180°. One coupling side end of one thread 10c is opposite a coupling side end of the other thread 10c with respect to the longitudinal axis L1. Accordingly, the respective fluid connection side ends of the threads 10c are also opposite each other with respect to the longitudinal axis L1.

In the disconnected state shown, the sealing member receptacle 20 is in a position with maximum distance to the fluid connection 12 and is retained in the coupling member housing 10 via two sealing member receptacle guiding structures 20a, each of which engages one of the threads 10c. The sealing member receptacle guiding structures 20a to be provided are primarily for guided movement of the sealing member receptacle 20 along the longitudinal axis L1 of a position of the sealing member receptacle 20 from a position with maximum distance to the fluid connection 12 to a position with minimum distance to the fluid connection 12, and vice versa. Accordingly, the sealing member 20 may also be retained in the coupling member housing 10 by other structural configurations, and the respective sealing member receptacle guiding structures 20a do not fully engage the respective threads 10c until the sealing member receptacle 20 moves along the longitudinal axis L1 toward the fluid connection 12.

In addition, the sealing member receptacle 20 comprises, at its end facing the coupling side 13, two exemplary fastening structures 22 on the coupling member side with snap hooks 22a formed at the coupling side ends. Via the fastening structures 22 with the snap hooks 22a, a mating coupling member 200 described later, as shown for example in FIG. 4, may be retained in predetermined positional relationship to the coupling member 100. The fastening structure according to FIG. 1 allows good accessibility to the coupling side front surface formed by the sealing member receptacle 20 and the sealing member 21, so that the latter may be disinfected without significant restrictions.

The sealing member 21 is arranged and dimensioned in the sealing member receptacle 20 such that, in a disconnected state, it completely surrounds, i.e. seals, a fluid opening 31 arranged in an end portion of the spike 30 facing the coupling side 13.

The movement of the sealing member receptacle 20 from a position with maximum distance to the fluid connection 12 toward a position with minimum distance to the fluid connection 12, or vice versa, is performed by the guidance of the respective sealing member receptacle guiding structures 20a in the respective threads 10c toward the fluid connection 12 or in the opposite direction thereto depending on the direction of movement to be provided. For this purpose, the housing portion 10a and/or the sealing member receptacle 20 may be selectively set into a rotational movement. This corresponds to an intentional screwing in or unscrewing. Alternatively or in addition, however, the application of a compressive or tensile force as a function of the direction of movement to be envisaged may be sufficient if the housing portion 10a and/or the sealing member receptacle 20 are rotatably supported in such a way that the housing portion 10a and/or the sealing member receptacle 20 thereby autonomously screws in or unscrews.

Figure 2:
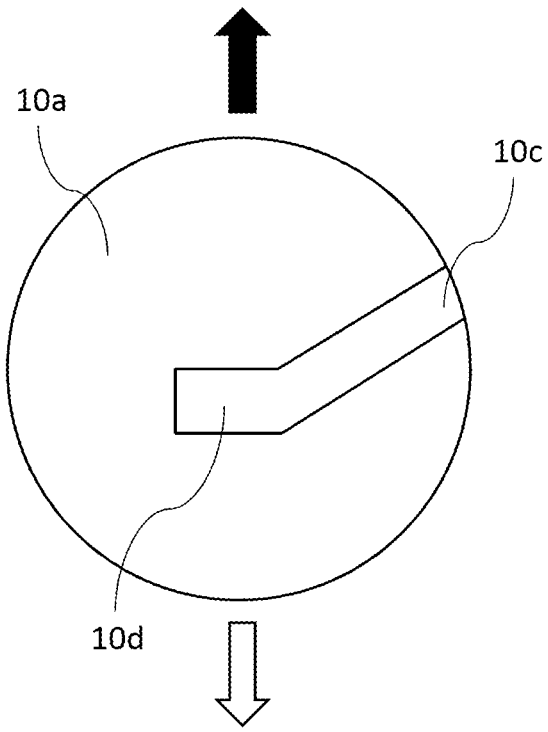
FIG. 2 is a section of an exemplary end of a fluid connection side thread with an orthogonal portion in a top view in a viewing direction on the longitudinal axis.
Figure 3:
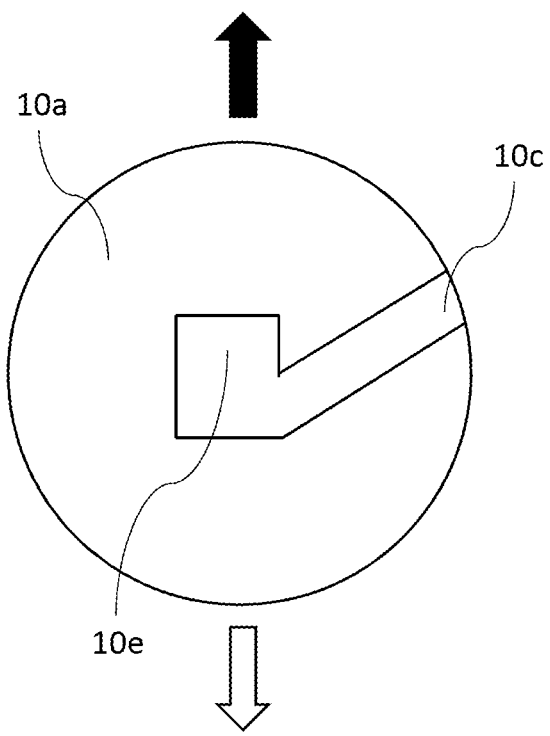
FIG. 3 is a section of another exemplary end of a thread on the fluid connection side with a recessed portion in a top view in a viewing direction on the longitudinal axis.

Insofar as autonomous screwing in or unscrewing is possible in principle, or also for other securing considerations, it may be advantageous to secure a position of the respective sealing member receptacle guiding structures 20a in the respective threads 10c in a position corresponding to a position with minimum distance to the fluid connection 12 against an unintentional change of position. Possible exemplary embodiments for such positional securing are shown in FIGS. 2 and 3, each of which shows a section of one end of a fluid connection side thread 10c in a top view viewing in the direction on the longitudinal axis L1. In each case, the filled arrow represents a longitudinal axis direction toward the coupling side 13, while the non-filled arrow represents a longitudinal axis direction toward the fluid connection 12.

FIG. 2 illustrates an exemplary end of a fluid connection side thread 10c with an orthogonal portion 10d with respect to the longitudinal axis L1. When a sealing member receptacle guiding structure 20a is moved into the orthogonal portion 10d, an applied compressive or tensile force does not cause rotational movement of the housing portion 10a and/or the sealing member receptacle 20. Accordingly, the risk of an unintended movement is reduced.

Alternatively, FIG. 3 shows an exemplary end of a fluid connection side thread 10c with a recessed portion 10e in the direction of the filled arrow. When a sealing member receptacle guiding structure 20a is moved into the recessed portion 10e, the position of the sealing member receptacle 20 is secured against rotational movement thereby. This position of the sealing member receptacle guiding structure 20a corresponds to a position of the sealing member receptacle 20 in a connected state, in which the sealing member receptacle 20 is in the position with minimum distance to the fluid connection 12 of the coupling member 100. Strictly speaking, the position of the sealing member receptacle 20 with minimum distance to the fluid connection 12 is formed by the position of the transition between the portion of the thread 10c still comprising an inclination and the recessed portion 10e. However, since the reverse offset is insignificant at the application scale, the position of the sealing member receptacle 20 when the sealing member guiding structure 20a engages the recessed portion 10e is also understood to be the position with minimum distance to the fluid connection 12.

To release the position securing via the recessed portion 10e, the sealing member receptacle guiding structure 20a must first be moved again relatively in the direction of the fluid connection 12 in order to be able to overcome the recessed portion 10e. This form of position securing is further supported by the provision of the elastic member 40. However, the position securing according to FIG. 3 does not exclude a position securing according to FIG. 2, so that a combined position securing may also be applicable.

FIG. 4 shows a schematic cross-sectional view of a mating coupling member 200 in a plane parallel to a mating coupling member longitudinal axis L2 of a mating coupling member housing 50 according to an exemplary first embodiment of the mating coupling member 200 in the disconnected state. The mating coupling member 200 comprises the mating coupling member housing 50 having a mating coupling member fluid connection 51 and a mating coupling side 52, wherein the mating coupling member housing 50 comprises the mating coupling member longitudinal axis L2 extending from the mating coupling member fluid connection 51 toward the mating coupling side 52. In addition, the mating coupling member comprises a sealing member 60 arranged at an end of the mating coupling member 200 facing the mating coupling side 52 in the mating coupling member housing 50 and forming, together with the mating coupling member housing 50, a mating coupling side front surface of the mating coupling member 200. The mating coupling member sealing member 60 seals, on the mating coupling side, a mating coupling member fluid channel 56 extending from the mating coupling member fluid connection 51 toward the mating coupling side 52, the mating coupling member fluid channel 56 extending coaxially with the mating coupling member longitudinal axis L2 in this example.

The mating coupling member housing 50 comprises a fastening portion 53 which extends from the mating coupling member side 52 in the direction of the mating coupling member longitudinal axis L2 toward the mating coupling member fluid connection 51 and comprises a mating coupling member side fastening structure 54, here, for example, two recesses 54a, for connection to the coupling member side fastening structure 22. In the embodiment shown, the recesses 54a are formed only in sections and correspond to the position and dimensioning of the snap hooks 22a of the fastening structures 22 of the mating coupling member 100 according to FIG. 1. Accordingly, the mating coupling member 200 may here be connected to the coupling member 100 according to FIG. 1 only in two with respect to the mating coupling member longitudinal axis L2.

In addition, the mating coupling member housing 50 comprises two unlocking mechanisms 55 on an external wall 50a extending in the direction of the mating coupling member longitudinal axis L2, via which the connection of the mating coupling member side fastening structure 54 to the coupling member side fastening structures 22 of the coupling member 100 is releasable as shown in FIG. 1. In the embodiment shown, the unlocking mechanisms 55 are each housing portions elastically supported on the external wall 50a, in which a portion facing the mating coupling side 52 and comprising the recess 54a is moved radially outwardly, i.e., in opposition to the mating coupling member longitudinal axis L2, by a radial pressure from the outside in the direction of the mating coupling member longitudinal axis L2. A snap hook engaging in the recess 54a would thus also be moved radially outwardly, so that a connection may be released.

Figure 6:
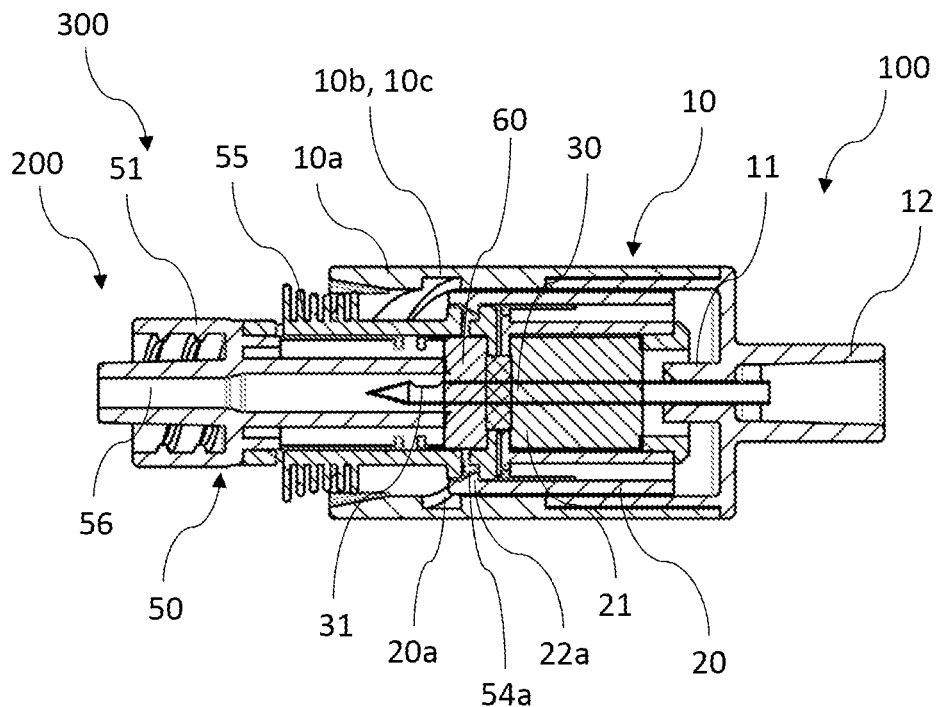
FIG. 6 is a schematic cross-sectional view of a coupling system according to FIG. 5 in a plane parallel to the longitudinal axis in the connected state.

With reference to FIGS. 5 and 6, the interaction of the coupling member 100 with a mating coupling member 200 in a coupling system 300 is described below.

For this purpose, FIG. 5 shows a schematic cross-sectional view of a coupling system 300 with a coupling member 100 according to FIG. 1 and a mating coupling member 200 according to FIG. 4 in a plane parallel to the longitudinal axis L1 or mating coupling member longitudinal axis L2 in the disconnected state. For reasons of simplicity, the respective longitudinal axes L1 or L2 as well as the elastic member 40 are not drawn in here. For this purpose, reference is made to FIGS. 1 and 4.

In the disconnected state shown, snap hooks 22a are in engagement with recesses 54a, so that the mating coupling member 200 is retained by the coupling member 100. Nevertheless, the coupling system 300 provides a disconnected state since the sealing member receptacle 20 is positioned with maximum distance to the fluid connection 12 which does not allow fluid communication between the coupling member 100 and mating coupling member 200. As a result of the engagement of the snap hooks 22a in the recesses 54a, the mutually facing front surfaces of the sealing member 21 and the mating coupling sealing member 60 are pressed against each other with a constant surface pressure in a fluid-tight manner. The fluid opening 31 arranged parallel to the longitudinal axis L1 is sealed by the sealing member 21.

In this regard, FIG. 6 shows a schematic cross-sectional view of a coupling system 300 according to FIG. 5 in a plane parallel to the longitudinal axis L1 or mating coupling member longitudinal axis L2 in the connected state. Again, for simplicity, the respective longitudinal axes L1 or L2 and the elastic member 40 are not drawn and reference is made accordingly to FIGS. 1 and 4.

By rotating the mating coupling member sealing receptacle 20, for example via rotation of the mating coupling member 100, in the direction of the threads 10c up to a fluid connection side end of the threads 10c, the mating coupling member sealing receptacle 20 is in a position with a minimal distance to the fluid connection 12. This position corresponds to a connected state in which the fluid opening 31 projects into the fluid channel 60 via the side of the mating coupling member sealing member 60 facing the mating coupling member fluid connection 51, thus forming a fluid communication.

In this embodiment, the housing portion 10a is configured such that the snap hooks 22a abut an inner surface of the housing portion 10a facing the longitudinal axis L1 in the connected state. This secures the connection of the mating coupling member 200 to the coupling member 100, since they may not be released via the release mechanisms 55.

FIG. 7 shows in addition an overview of all external views of the coupling system according to FIGS. 4 and 5, the sectional views along intersection line A-A and intersection line B-B, and a perspective view in the disconnected state. This results in further design features of the described embodiment. Similarly, FIG. 8 shows an overview of the coupling system 300 according to FIG. 7 in a disconnected state, in which the mating coupling member 200 is retained by the coupling member 100, and FIG. 9 in a connected state.

The invention is not limited to the described embodiments. In particular, certain features of one embodiment are in principle applicable to other embodiments, unless reasonably precluded.

The invention claimed is:

1. A coupling member for a closed fluid transfer system, comprising:
    a coupling member housing comprising a fluid connection and a coupling side, wherein the coupling member housing comprises a longitudinal axis extending from the fluid connection toward the coupling side;
    a spike comprising at least one fluid opening and retained in a spike receptacle of the housing disposed at the fluid connection and extending in the direction of the longitudinal axis into the coupling member housing, wherein the at least one fluid opening is arranged in an end portion of the spike facing the coupling side;
    a sealing member receptacle arranged in the coupling member housing on the coupling side; and
    a sealing member arranged in the sealing member receptacle,
    wherein the coupling housing comprises a housing portion, which at least partially surrounds the sealing member receptacle in an axial direction with respect to the longitudinal axis and comprises a coupling housing threaded portion on the inner surface facing the sealing member, and
    wherein the coupling housing with the sealing member is, guided by a sealing member receptacle guiding structure, movable in the direction of the longitudinal axis via the coupling housing threaded portion between a position with maximum distance to the fluid connection and a position with minimum distance to the fluid connection, and
    wherein the housing portion is rotatable relative to the longitudinal axis.

2. The coupling member according to claim 1, wherein the at least one fluid opening is arranged in the sealing member, when the sealing member receptacle with the sealing member is located in the position with maximum distance to the fluid connection.

3. The coupling member according to claim 1, wherein the coupling housing threaded portion is formed as female thread, and the sealing member receptacle guiding structure comprises at least one projection engageable in the female thread projecting radially outward with respect to the longitudinal axis.

4. The coupling member according to claim 1, wherein the coupling housing threaded portion comprises at least two threads separated from each other.

5. The coupling member according to claim 4, wherein the at least two threads are opposing each other.

6. The coupling member according to claim 1, wherein at least one thread of the coupling housing threaded portion extends over an angle of less than 360° with respect to the longitudinal axis.

7. The coupling member according to claim 6, wherein at least one thread of the coupling housing threaded portion extends over an angle of substantially 180° with respect to the longitudinal axis.

8. The coupling member according to claim 1, wherein at least one thread of the coupling housing threaded portion comprises, at its end facing the fluid connection, an orthogonal portion with respect to the longitudinal axis.

9. The coupling member according to claim 1, wherein at least one thread of the coupling housing threaded portion comprises, at its end facing the fluid connection, a recessed portion toward the longitudinal axis, which is recessed in the direction of the coupling side with respect to the thread.

10. The coupling member according to claim 1, wherein the sealing member receptacle is rotatable relative to the longitudinal axis and/or to the coupling member housing.

11. The coupling member according to claim 1, wherein the sealing member receptacle, together with the sealing member, forms at least a part of the coupling side front surface of the coupling member.

12. The coupling member according to claim 1, wherein the sealing member receptacle comprises, at its end facing the coupling side, a coupling member side fastening structure for a mating coupling member.

13. The coupling member according to claim 12, wherein the coupling member side fastening structure for the mating coupling member is formed by at least two snap hooks projecting in the direction of the longitudinal axis toward the coupling side.

14. The coupling member according to claim 1, wherein the sealing member receptacle is supported in the coupling member housing by an elastic member.

15. The coupling member according to claim 14, wherein the elastic member is a compression spring member, which acts in the direction of the longitudinal axis and is arranged between the fluid connection and the sealing member receptacle.

16. A coupling system for the closed fluid transfer system, comprising at least one coupling member according to claim 1 and at least one mating coupling member, wherein the mating coupling member comprises:
    a mating coupling member housing comprising a mating coupling member fluid connection and a mating coupling side, wherein the mating coupling member housing comprises a mating coupling member longitudinal axis extending from the mating coupling member fluid connection toward the mating coupling side; and
    a mating coupling member sealing member, which is arranged in the mating coupling member housing and forms, together with the mating coupling member housing, at least a part of a mating coupling side front surface of the mating coupling member, wherein the coupling system is configured such that the fluid opening of the coupling member in a state connected to the mating coupling member, in which the sealing member receptacle is located in the position with minimum distance to the fluid connection of the coupling member, is at least partially arranged on a side of the mating coupling member sealing member of the mating coupling member facing the mating coupling member fluid connection.

17. The coupling system according to claim 16, wherein the mating coupling member housing comprises a fastening portion, which extends from the mating coupling side in the direction of the mating coupling member longitudinal axis toward the mating coupling member fluid connection and comprises a mating coupling member side fastening structure for connection to a coupling member side fastening structure.

18. The coupling system according to claim 17, wherein the mating coupling member housing comprises an unlocking mechanism on an external wall extending in the direction of the mating coupling member longitudinal axis, by which the connection of the mating coupling member side fastening structure to the coupling member side fastening structure is releasable.

19. The coupling member according to claim 17, wherein the mating coupling member side fastening structure for connection to the coupling member side fastening is a recess for receiving snap hooks.

* * * * *